US011059774B2

(12) United States Patent
Chi et al.

(10) Patent No.: US 11,059,774 B2
(45) Date of Patent: Jul. 13, 2021

(54) PROCESSES AND SYSTEMS FOR USING SILICA PARTICLES IN FLUID BED REACTOR

(71) Applicant: Ascend Performance Materials Operations LLC, Houston, TX (US)

(72) Inventors: Yawu T. Chi, Sugar Land, TX (US); James Sutton, Houston, TX (US); Ali Akhavan, Houston, TX (US); Celia L. Kniepmann, Houston, TX (US); Matthew D. Cox, Pearland, TX (US); Valerie S. Monical, League City, TX (US)

(73) Assignee: Ascend Performance Materials Operations LLC, Houston, TX (US)

( * ) Notice: Subject to any disclaimer, the term of this patent is extended or adjusted under 35 U.S.C. 154(b) by 0 days.

(21) Appl. No.: 16/455,366

(22) Filed: Jun. 27, 2019

(65) Prior Publication Data

US 2020/0002271 A1 Jan. 2, 2020

Related U.S. Application Data

(60) Provisional application No. 62/691,225, filed on Jun. 28, 2018.

(51) Int. Cl.
*C07C 253/18* (2006.01)
*B01J 8/00* (2006.01)
(Continued)

(52) U.S. Cl.
CPC .......... *C07C 253/18* (2013.01); *B01J 8/0025* (2013.01); *B01J 8/0055* (2013.01); *B01J 8/1827* (2013.01);
(Continued)

(58) Field of Classification Search
None
See application file for complete search history.

(56) References Cited

U.S. PATENT DOCUMENTS 3,164,626 A 1/1965 Saburo et al.
3,335,169 A 8/1967 Eden
(Continued)

FOREIGN PATENT DOCUMENTS

CN 103269790 8/2013
CN 107983335 5/2018
(Continued)

OTHER PUBLICATIONS

Armor ("Silica as an Oxidation Catalyst" Journal of Catalysis, 73, 57-65, 1982) (Year: 1982).*
(Continued)

*Primary Examiner* — Amy C Bonaparte
(74) *Attorney, Agent, or Firm* — Cozen O'Connor

(57) ABSTRACT

The present disclosure relates to fluid bed processes that utilize silica particles as a fluidization aid. The process comprises reacting one or more reactants in a reactor comprising a fluid bed to form a product. The fluid bed comprises a catalyst composition comprising a catalyst and an inert additive composition comprising silica particles from 0.5 wt % to 30 wt %, based on the total weight of the catalyst composition. The silica particles are discrete, inert particles that are mixed with the catalyst in the fluid bed.

15 Claims, 1 Drawing Sheet

(51) Int. Cl.
   *B01J 8/18* (2006.01)
   *C07C 253/24* (2006.01)

(52) U.S. Cl.
   CPC ............ *B01J 8/1863* (2013.01); *C07C 253/24* (2013.01); *B01J 2208/00805* (2013.01); *B01J 2208/00991* (2013.01)

(56) References Cited

U.S. PATENT DOCUMENTS

| | | | |
|---|---|---|---|
| 3,446,834 A | | 5/1969 | Cavaterra et al. |
| 3,668,147 A | | 6/1972 | Yoshino et al. |
| 4,018,712 A | | 4/1977 | Li |
| 4,225,531 A | * | 9/1980 | Jones |
| 4,590,011 A | | 5/1986 | Li |
| 5,079,379 A | | 1/1992 | Braun et al. |
| 6,384,156 B1 | * | 5/2002 | Bernier ............... B01J 8/1827 526/136 |
| 6,916,763 B2 | | 7/2005 | Tway |
| 2005/0245781 A1 | * | 11/2005 | Martens ............... B01J 8/0025 585/640 |

FOREIGN PATENT DOCUMENTS

| | | |
|---|---|---|
| EP | 0145692 A | 6/1985 |
| GB | 1474258 A | 5/1977 |
| WO | 9739300 A1 | 10/1997 |

OTHER PUBLICATIONS

Grasselli ("Advances and future trends in selective oxidation and ammoxidation catalysts", Catalysis Today, 49, 1999, p. 141-153) (Year: 1999).*

Taiwanese Application No. 108122972, "Office Action", dated Apr. 8, 2020, 4 pages.

International Application No. PCT/US2019/039563, "International Search Report and Written Opinion", dated Jan. 2, 2020, 17 pages.

International Application No. PCT/US2019/039563, "Invitation to Pay Additional Fees and, Where Applicable, Protest Fee", dated Oct. 28, 2019, 12 pages.

* cited by examiner

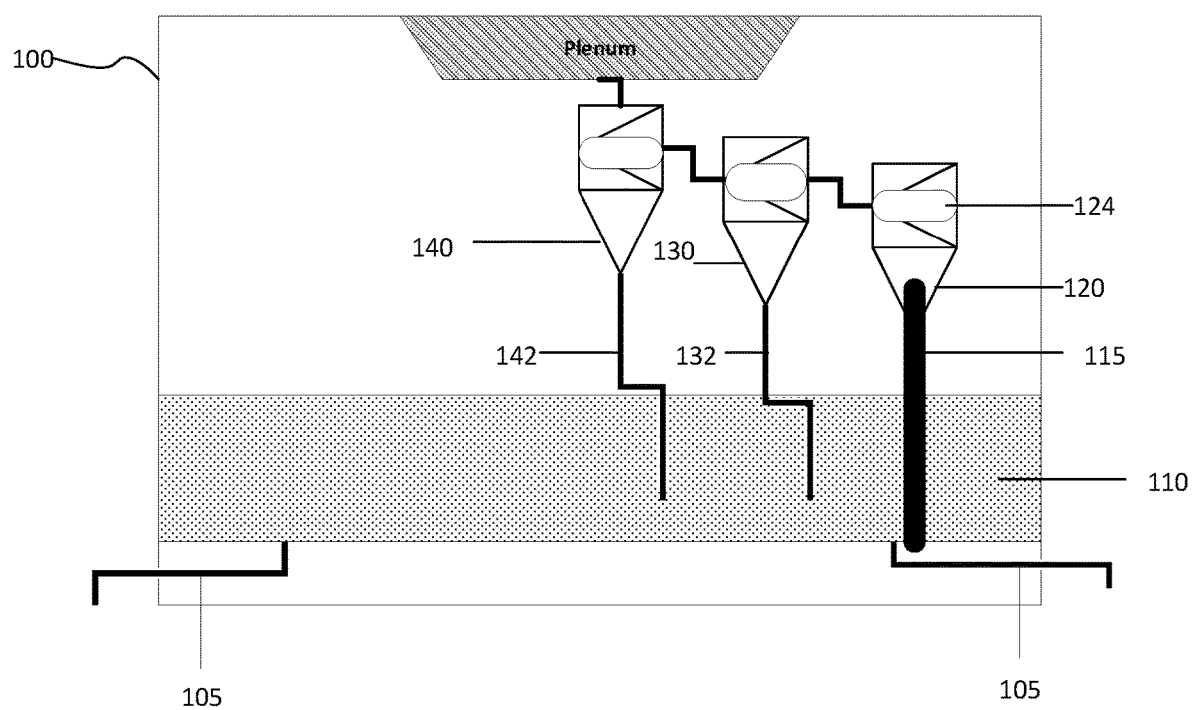

PROCESSES AND SYSTEMS FOR USING SILICA PARTICLES IN FLUID BED REACTOR

CROSS-REFERENCE TO RELATED APPLICATION

This application claims the benefit of and the priority to U.S. Provisional Application No. 62/691,225, filed on Jun. 28, 2018, which is hereby incorporated by reference in its entirety for all purposes.

FIELD

The present disclosure relates to fluid bed reactors. More specifically, the present disclosure relates to fluid bed reactors that utilize an inert additive composition comprising silica particles as a fluidization aid.

BACKGROUND

Some processes for fluidizing a particulate catalyst in a fluid bed reactor are well known. In these processes, a gaseous reactant stream contacts the catalyst in the fluid bed to convert reactants to desired reaction products. Typically, some catalyst, e.g., small particles thereof, becomes entrained in the product stream and must be separated from the product stream after it exits the fluid bed. This is commonly accomplished by a particle separation system located downstream of the fluid bed to separate the catalyst from the product stream. Unfortunately, during the fluidization process, a portion of the catalyst is converted to dust and exits the system with the product stream. Additionally, even with a particle separation system, a portion of the catalyst becomes entrained and lost in the product stream.

In some processes, the fluid bed may include a fluidization aid, e.g., alumina, to reduce the catalyst loss. The fluidization aid may be mixed with the catalyst in the fluid bed and the gaseous reactants pass through and fluidize a bed of catalyst and fluidization aid. Products, byproducts, unreacted reactants, and entrained particulates of catalyst and fluidization aid exit the fluid bed and are directed to the particle separation systems. The particle separation system separates and recovers a major portion of the particulates while the gaseous product stream passes overhead for further processing, e.g., purification, utilization, or packaging. Conventional fluidization aids used in fluid bed reactors, however, are more dense, harder, and are more roughly shaped than the catalyst which results in increased erosion of the reactor. When erosion rates are high, there is higher chance of premature failure of the reactor leading to high catalyst losses.

For example, U.S. Pat. No. 5,079,379 discloses the use of particulate inert fines, e.g., alumina particles, to reduce solids losses and particulate catalyst losses in fluidized bed catalytic reactors.

The problem is particularly apparent in ammoxidation processes where catalysts of relatively small particle sizes are frequently used. Such processes are disclosed, for example, in U.S. Pat. Nos. 3,164,626; 3,335,169; 3,446,834; 3,668,147; and 4,018,712; and 4,590,011; the teachings of which are incorporated herein by reference. U.S. Pat. No. 4,590,011 discloses process for the ammoxidation of hydrocarbons to unsaturated nitriles using a fluidized bed containing a mixture of active catalyst and discrete particles of an inert material to improve the yield of nitriles and inhibit the formation of by-products.

Although some references may teach the use of inert particulates in fluid bed process, the need still exists for improved fluid bed processes that reduce catalyst loss and improve product yield without contributing to reactor erosion.

The references identified herein are hereby incorporated by reference.

SUMMARY

In some embodiments, the present disclosure relates to a process comprising: reacting one or more reactants in a reactor comprising a fluid bed to form a product; wherein the fluid bed comprises a catalyst composition comprising a catalyst and an inert additive composition comprising from 0.5 wt % to 30 wt % of silica particles, based on the total weight of the catalyst composition, wherein the silica particles have an equivalent median particle diameter ranging from 10 microns to 500 microns. In some aspects, the catalyst comprises one or more of antimony, uranium, iron, bismuth, vanadium, molybdenum, nickel, potassium, cobalt, oxides thereof, or salts thereof. In some aspects, the catalyst has an equivalent median diameter ranging from 1 microns to 125 microns. In some aspects, the silica particles have a real density ranging from 1.8 $g/cm^3$ to 2.8 $g/cm^3$, and wherein the difference between the density of the silica particles and the catalyst is less than 75%. In some aspects, the silica particles have a surface area less than 50 $m^2/g$, and wherein the silica particles have a hardness ranging from 500 to 720 as measured by ASTM E384 (2018). In some aspects, the silica particles have a sphericity ranging from 60% to 99.9%. In some aspects, the catalyst composition further comprises alumina particles, wherein a weight ratio of alumina particles to silica particles is less than 1:1. In some aspects, the inert additive composition comprises no alumina. In some aspects, the process reduces consumption of the catalyst by greater than 5% per kilogram of product produced compared to other fluidization aids. In some aspects, the silica particles reduce erosion of the reactor by greater than 10% compared to a similar process conducted without from 0.5 wt % to 30 wt % silica particles. In some aspects, the process demonstrates a product yield greater than 0.2% greater than that of a similar process conducted without from 0.5 wt % to 30 wt % silica particles. In some aspects, the silica particles have a real density ranging from 2.1 $g/cm^3$ to 2.5 $g/cm^3$, wherein the silica particles have a surface area less than 1 $m^2/g$, wherein the silica particles have a hardness ranging from 500 to 720 as measured by ASTM E384 (2018), and wherein the product yield is greater than 70%. In some aspects, the silica particles have an equivalent median particle diameter ranging from 20 microns to 100 microns, wherein the silica particles have a real density ranging from 2.1 $g/cm^3$ to 2.5 $g/cm^3$, wherein the silica particles have a sphericity greater than 67%, wherein the silica particles comprise greater than 99 wt % silica, wherein the product yield is greater than 70%.

In some embodiments, the present disclosure relates to a process for producing acrylonitrile product, the process comprising: reacting one or more reactants in a reactor comprising a fluid bed to form an acrylonitrile product; wherein the fluid bed comprises a catalyst composition comprising a catalyst and an inert additive composition comprising silica particles having a density from 1.8 $g/cm^3$ to 2.8 $g/cm^3$, wherein the silica particles have a sphericity ranging from 60% to 99.9%. In some aspects, the difference between the density of the silica particles and the catalyst is less than 75%, wherein the process demonstrates an acrylonitrile product yield greater than 0.2% greater than that of a similar process conducted without silica particles. In some aspects, the one or more reactants comprises an olefin, ammonia, and an oxygen-containing gas.

In some embodiments, the present disclosure relates to a reactor system for preparing acrylonitrile product, comprising: a fluid bed comprising a catalyst composition comprising a catalyst and an inert additive composition comprising from 0.5 wt % to 30 wt % of silica particles, based on the total weight of the catalyst composition; and one or more gas inlet feeds for passing one or more reactants upwardly through the fluid bed to form an acrylonitrile product, wherein the difference between the density of the silica particles and the catalyst particles ranges from 0.5% to 75%, wherein the silica particles reduce erosion of the reactor by greater than 10% compared to a similar process conducted without from 0.5 wt % to 30 wt % silica particles. In some aspects, the silica particles have a real density ranging from 1.8 g/cm$^3$ to 2.8 g/cm$^3$, wherein the silica particles have a surface area less than 50 m$^2$/g, wherein the silica particles have a hardness ranging from 500 to 720 as measured by ASTM E384 (2018), and wherein the product yield is greater than 70%. In some aspects, the process demonstrates an acrylonitrile product yield greater than 0.2% greater than that of a similar process conducted without from 0.5 wt % to 30 wt % silica particles. In some aspects, the reactor system further comprises: one or more gas inlet feeds for passing the one or more reactants upwardly through the fluid bed; and one or more cyclones to separate particles from the gas flowing upwardly through the fluid bed of the reactor, the cyclones being in communication with the upwardly flowing gas exiting the fluid bed, wherein the one or more cyclones comprise a particle discharge pipe for returning separated particles to the fluid bed.

BRIEF DESCRIPTION OF THE DRAWING

The FIGURE shows a schematic diagram of a fluid bed reactor system including cyclones according to embodiments of the present disclosure.

DETAILED DESCRIPTION

Introduction

The present disclosure relates to the use of an inert additive composition comprising silica particles as a fluidization aid in a fluid bed reactor. The inert additive composition may be mixed with catalyst in the fluid bed to improve product yield, reduce catalyst loss, and reduce erosion of the reactor. It has been found that catalyst consumption, e.g., catalyst loss, in a system having a fluid bed reactor, e.g., the cyclone(s) thereof, and optionally a particulate separation system, e.g., cyclones, downstream of the fluid bed reactor, is significantly reduced when the catalyst is mixed with an inert additive composition including silica particles.

Conventionally, fluid bed processes have utilized alumina as a fluidization aid to improve product yield and inhibit formation of by-products. However, although the use of alumina may reduce catalyst loss compared to processes that do not use a fluidization aid, higher quantities of alumina often reduce the number of reactions per catalyst charge, which adversely affects the overall efficiency of the process. Also, in some instances, alumina has been found to contribute to (among others) the problems of reactor erosion, e.g., erosion in the cyclone system, which also reduces the efficiency of the process. Generally speaking, fluid bed processes that utilize alumina particles have been shown to consume greater amounts of catalyst without achieving higher product yields and selectivity.

It has been found that using silica particles as fluidization aids, e.g., instead of alumina, significantly reduces catalyst loss and reactor erosion in fluid bed processes. In some aspects, the silica particles have a specific shape, e.g., spherical, and particle size distribution that promotes improved product yields and inhibits formation of byproducts compared to conventional processes. The specific weight percentage of silica particles in the fluid bed, as well as the density and particle shape and/or size of the silica particles, contribute to increased conversion of the reactants and overall yield of the process. Without being bound by theory, it is believed that the density and/or the specific particle size distribution of the silica particles surprisingly retards reactor erosion. In particular, the use of silica particles in fluid bed reactors that have a separation system, e.g., cyclones, downstream from the fluid bed, has been found to have unexpected erosion reduction benefits.

Alumina particles have high densities as compared to the respective catalyst used in the fluid bed. It is postulated that this high density/density difference reduces the life of the reactor due to erosion, which leads to catalyst loss. Also, the specific particle size distribution of alumina used in fluid bed processes has been found to contribute to erosion of the reactors thereby reducing the amount of catalyst used per charge of the reactor. The inventors have discovered that the use of silica particles, e.g., with the specific density and particle size distribution, surprisingly and unexpectedly contributes to process improvements, e.g., product yield, catalyst loss, reactor erosion, and erosion of other units in the process, e.g., separation units.

Moreover, silica particles used in fluid bed processes are provided in a specific ratio of catalyst to fluidization aid that beneficially prevents loss of catalyst compared to an otherwise identical system that utilizes another fluidization aid, e.g., alumina particles.

In some cases, the silica particles are inert and discrete particles. The silica particles may be physically mixed with the catalyst in the fluid bed. As used herein, the term "discrete" refers to particles separate from and not being a part of the catalyst particle. That is, catalyst support material and deactivated catalyst (unless present as separate particles) are not considered as constituting any portion of the inert additive composition. The term "inert" refers to particles that do not significantly catalytically or chemically react with the reactants and/or the products in the fluid bed reactor. In some aspects, the silica particles can be any form of silica provided to the fluid bed reactor as an additive, e.g., fines, particles, compounds, ions, or mixtures thereof. For example, the silica particles may be silica fines.

In some embodiments, the present disclosure is related to processes that utilize a reactor comprising a fluid bed including a catalyst composition comprising a catalyst and an inert additive composition comprising silica particles. The silica particles may have an equivalent median particle diameter ranging from 10 microns to 500 microns. The silica particles may be mixed with the catalyst particles in the fluid bed. A feedstock, e.g., reactants, contacts the catalyst composition and inert additive composition in the fluid bed under conditions effective to convert greater than a portion of the feedstock to product. The reactor may, in some embodiments, have one or a plurality of cyclones.

In some embodiments, the present disclosure is related to a process for the ammoxidation of propylene to acrylonitrile. The process includes charging a feed comprising propylene, ammonia and oxygen to a fluidized bed operated at ammoxidation conditions. The fluid bed comprising a catalyst composition comprising an active ammoxidation catalyst and an inert additive composition comprising silica particles. The silica particles are discrete, inert particles having a particle size distribution compatible with fluidization in the fluid bed. The process produces acrylonitrile which is withdrawn from the fluid bed. The resulting product, acrylonitrile, is recovered from the reaction zone of the fluid bed. The product may be separated to remove catalyst and/or filtration aid particulates. In some aspects, greater than some of the particulates are recirculated back to the fluid bed, e.g., from the bottom of the last cyclones of the reactor system to the fluid bed.

Catalyst Composition

The fluid bed comprises a catalyst composition. The catalyst composition may vary widely, and generally the catalyst composition can be used to carry out a variety of chemical reactions, e.g., multiphase reactions. In a fluid bed reactor, a fluid, e.g., gas or liquid, is passed through the catalyst composition at sufficient velocities to suspend the composition and cause it to behave as though it were a fluid. The catalyst composition may comprise a catalyst and an inert additive composition. In some embodiments, the catalyst composition comprises the total compositional weight of the fluid bed, e.g., the total weight of the catalyst and the inert additive composition.

In some embodiments, the inert additive composition does not unduly interfere with the fluidizing properties of the catalyst composition used in the fluid bed, and is inert, e.g., imparts no undesirable catalytic activity and has no undesirable chemical reactivity. In some embodiments, the inert additive composition has little or no catalytic activity and/or chemical reactivity compared to the catalyst particles.

The catalyst composition comprises an inert additive composition including silica particles. In some embodiments, the inert additive composition comprises silica particles ranging from 0.5 wt % to 30 wt %, e.g., from 1 wt % to 28 wt %, from 2 wt % to 26 wt %, from 4 wt % to 24 wt %, from 5 wt % to 22 wt %, from 6 wt % to 20 wt %, from 7 wt % to 18 wt %, from 8 wt % to 16 wt %, from 9 wt % to 14 wt %, or from 10 wt % to 12 wt %, where weight percentages are based on the total weight of the catalyst composition. In terms of upper limits, the inert additive composition may comprise less than 30 wt % of silica particles, e.g., less than 26 wt %, less than 22 wt %, less than 18 wt %, less than 14 wt %, less than 12 wt %, or less than 11 wt %. In terms of lower limits, the inert additive composition may comprise greater than 0.5 wt % of silica particles, e.g., greater than 1 wt %, greater than 2 wt %, greater than 4 wt %, greater than 6 wt %, greater than 8 wt %, or greater than 10 wt %.

In some embodiments, the inert additive composition comprises from 0.5 wt % to 99.99 wt % silica particles, e.g., from 1 wt % to 99.9 wt %, from 5 wt % to 99.5 wt %, from 10 wt % to 99 wt %, from 10 wt % to 98 wt %, from 20 wt % to 95 wt %, from 30 wt % to 90 wt %, from 40 wt % to 85 wt %, from 50 wt % to 80 wt %, from 60 wt % to 75 wt %, or from 65 wt % to 70, wherein weight percentages are based on the total weight of the inert additive composition. In terms of lower limits, the inert additive composition comprises greater than 0.5 wt % silica particles, e.g., greater than 1 wt %, greater than 5 wt %, greater than 10 wt %, greater than 20 wt %, greater than 30 wt %, greater than 40 wt %, greater than 50 wt %, or greater than 60 wt %. In terms of upper limits, the inert additive composition comprises less than 99.99 wt % silica particles, e.g., less than 99.9 wt %, less than 99.5 wt %, less than 99 wt %, less than 95 wt %, less than 90 wt %, less than 85 wt %, less than 80 wt %, or less than 75 wt %. In some embodiments, the inert additive composition comprises 99.99 wt % silica particles.

In some embodiments, the silica particles have an equivalent median particle diameter ranging from 10 microns to 500 microns, e.g., from 12 microns to 400 microns, from 14 microns to 300 microns, from 16 microns to 200 microns, from 18 microns to 100 microns, from 20 microns to 80 microns, from 22 microns to 60 microns, from 24 microns to 50 microns, from 26 microns to 40 microns, or from 28 microns to 36 microns. In terms of upper limits, the silica particles have an equivalent median diameter less than 500 microns, e.g., less than 400 microns, less than 300 microns, less than 200 microns, less than 150 microns, less than 100 microns, or less than 80 microns. In terms of lower limits, the silica particles have an equivalent median diameter greater than 10 microns, e.g., greater than 12 microns, greater than 15 microns, greater than 20 microns, greater than 25 microns, greater than 30 microns, greater than 35 microns, or greater than 40 microns. The equivalent median particle diameter is the diameter of an irregularly-shaped object for a sphere of an equivalent volume.

The inert additive composition may be combined with the catalyst before addition to the fluid bed. In other cases, the inert additive composition and catalyst can be added separately to the fluid bed. In some aspects, the inert additive composition is mixed in the fluid bed independent of the catalyst. In some aspects, the inert additive composition is provided in the fluid bed before the catalyst is added to fluid bed. In other aspects, the inert additive composition is physically mixed with the catalyst before being supplied to the fluid bed.

In some aspects, the silica particles, as a whole, may comprise one or more impurities. As used herein, the term "impurities" refers to atoms or molecules other than silica that are provided with the silica particles, e.g., fused with the silica. In some aspects, the silica particles may include one or more impurities comprising aluminum, iron, nickel, sodium, boron, calcium, copper, cadmium, magnesium, boron, potassium, phosphorus, and oxides thereof. In some aspects, the silica particles comprise one or more of $Al_2O_3$, $Fe_2O_3$, $Na_2O$, $K_2O$, CaO, and MgO.

In some embodiments, the silica particles comprise $SiO_2$ ranging from 80 wt % to 100 wt %, e.g., from 85 wt % to 99.9 wt %, from 88 wt % to 99.5 wt %, from 92 wt % to 99 wt %, from 94 wt % to 98 wt %, or from 95 wt % to 99 wt %, wherein the weight percentage are based on the total weight of the silica particles. In terms of lower limits, the silica particles comprise greater than 80 wt % $SiO_2$, e.g., greater than 82 wt %, greater than 84 wt %, greater than 88 wt %, greater than 94 wt %, greater than 94 wt %, or greater than 96 wt %. In terms of upper limits, the silica particles comprise less than 100 wt % $SiO_2$, e.g., less than 99.9 wt %, less than 99.6 wt %, less than 99.2 wt %, less than 99 wt %, less than 98.8 wt %, or less than 98.5 wt %.

In some embodiments, the silica particles comprise impurities ranging from 0.01 wt % to 20 wt %, e.g., from 0.05 wt % to 15 wt %, from 0.1 wt % to 10 wt %, from 0.2 wt % to 5 wt %, from 0.4 wt % to 1 wt %, or from 0.5 wt % to 0.8 wt %, wherein the weight percentage are based on the total weight of the silica particles. In terms of upper limits, the silica particles comprise less than 20 wt % of impurities, e.g., less than 18 wt %, less than 16 wt %, or less than 14 wt %, less than 12 wt %, less than 10 wt %, less than 8 wt %, less than 6 wt %, or less than 4 wt %. In terms of lower limits, the silica particles comprise greater than 0.01 wt % impurities, e.g., greater than 0.04 wt %, greater than 0.08 wt %, greater 0.1 wt %, greater than 0.5 wt %, greater than 1 wt %, greater than 2 wt %, or greater than 3 wt %.

In some embodiments, the silica particles comprise nickel ranging from 1 ppm to 150 ppm, e.g., from 10 ppm to 140 ppm, from 20 ppm to 120 ppm, from 30 ppm to 100 ppm, from 40 ppm to 80 ppm, or from 50 ppm to 70 ppm. In terms of upper limits, the silica particles comprise less than 150 ppm of nickel, e.g., less than 145 ppm, less than 140 ppm, less than 120 ppm, less than 100 ppm, less than 80 ppm, less than 60 ppm, or less than 50 ppm. In terms of lower limits, the silica particles comprise greater than 1 ppm of nickel, e.g., greater than 5 ppm, greater than 10 ppm, greater than 20 ppm, greater than 25 ppm, greater than 30 ppm, greater than 40 ppm, or greater than 45 ppm.

In some embodiments, the silica particles comprise iron ranging from 1 ppm to 180 ppm, e.g., from 10 ppm to 160 ppm, from 20 ppm to 140 ppm, from 30 ppm to 120 ppm, from 40 ppm to 100 ppm, or from 60 ppm to 80 ppm. In terms of upper limits, the silica particles comprise less than 180 ppm of iron, e.g., less than 160 ppm, less than 140 ppm, less than 120 ppm, less than 100 ppm, less than 80 ppm, or less than 60 ppm. In terms of lower limits, the silica particles comprise greater than 1 ppm of iron, e.g., greater than 5 ppm, greater than 10 ppm, greater than 20 ppm, greater than 25 ppm, greater than 30 ppm, greater than 40 ppm, or greater than 50 ppm.

The silica particles may have a wide variety of shapes or combination of different shapes. In some embodiments, silica particles can be spherical particles, ellipsoidal particles, cubic particles, rectangular particles, angular particles, and any combination thereof. According to certain embodiments, the silica particles are generally spherical particles. Further, the silica particles may be selected from hollow particles and solid particles, and any combination thereof. In some aspects, the silica particles may have no defined shape, e.g., substantially globular. The inventors have found that the specific particle size of the silica particles beneficially improves fluidization of the catalyst composition which increases overall product yield and conversion.

In some embodiments, the silica particles have a sphericity ranging from 60% to 99.9%, e.g., from 65% to 99%, from 70% to 95%, from 75% to 90%, from 80% to 90%, from 85% to 95%, or from 90% to 100%. In terms of lower limits, the silica particles have a sphericity greater than 60%, e.g., greater than 65%, greater than 67%, greater than 70%, greater than 75%, greater than 80%, greater than 85%, greater than 88%, greater than 90%, or greater than 90.5%. In terms of upper limits, the silica particles have a sphericity of less than 99.9%, e.g., less than 99%, less than 98% less than 96%, less than 95%, less than 94%, less than 92%, or less than 91%.

In some embodiments, the average particle dimensions of the silica particles can have a generally single peaked distribution. For example, all particles could have the same average particle dimension or, as another example, the particles could have a distribution of average particle dimensions, such as a Gaussian distribution, so that the average particle dimensions range above and below some mean value.

In some embodiments, the average particle dimension of the silica particles may have a multimodal distribution. For example, the average particle dimensions may have a bimodal distribution or higher modal distributions, e.g., trimodal. A multimodal distribution of particle dimensions could be useful to, for example, tailor the fluidization properties of the catalyst composition. In addition to distributions of size, other particle features, such as, for example, particle shape, e.g., angular and spherical silica particles, and particle composition, may be distributed about a single mean or may have a multimodal distribution.

In some embodiments, the silica particles have a density ranging from 1.8 g/cm$^3$ to 2.8 g/cm$^3$, e.g., from 1.9 g/cm$^3$ to 2.7 g/cm$^3$, from 2.0 g/cm$^3$ to 2.6 g/cm$^3$, from 2.1 g/cm$^3$ to 2.5 g/cm$^3$, from 2.2 g/cm$^3$ to 2.4 g/cm$^3$, or from 2.25 g/cm$^3$ to 2.35 g/cm$^3$. In terms of upper limits, the silica particles have a density less than 2.8 g/cm$^3$, e.g., less than 2.75 g/cm$^3$, less than 2.7 g/cm$^3$, less than 2.6 g/cm$^3$, less than 2.5 g/cm$^3$, less than 2.4 g/cm$^3$, or less than 2.3 g/cm$^3$. In terms of lower limits, the silica particles have a density greater than 1.8 g/cm$^3$, e.g., greater than 1.9 g/cm$^3$, greater than 1.95 g/cm$^3$, greater than 2.0 g/cm$^3$, greater than 2.1 g/cm$^3$, greater than 2.2 g/cm$^3$, or greater than 2.25 g/cm$^3$. The inventors have found that the specific density of the silica particles is similar to the density of the catalyst which improves overall fluidization behavior.

In some embodiments, the difference between the density of the silica particles and the catalyst particles ranges from 0.5% to 75%, e.g., from 1% to 70%, from 2% to 60%, from 4% to 50%, from 6% to 40%, from 8% to 30%, or from 10% to 20%. In terms of upper limits, the difference between the density of the silica particles and the catalyst particles is less than 75%, e.g., less than 70%, less than 60%, less than 50%, less than 40%, less than 30%, or less than 25%. In terms of lower limits, the difference between the density of the silica particles and the catalyst particles is greater than 0.5%, e.g., greater than 1%, greater than 2%, greater than 4%, greater than 6%, greater than 8%, greater than 10%, or greater than 15%.

In some embodiments, the silica particles have a surface area ranging from 0.01 m$^2$/g to 50 m$^2$/g, e.g., from 0.05 m$^2$/g to 25 m$^2$/g, from 0.08 m$^2$/g to 20 m$^2$/g, from 0.1 m$^2$/g to 10 m$^2$/g, from 0.2 m$^2$/g to 5 m$^2$/g, 0.25 m$^2$/g to 1 m$^2$/g, or from 0.3 m$^2$/g to 0.6 m$^2$/g. In terms of upper limits, the silica particles have a surface area less than 50 m$^2$/g, e.g., less than 25 m$^2$/g, less than 10 m$^2$/g, less than 5 m$^2$/g, or less than 1 m$^2$/g, or less than 0.5 m$^2$/g. In terms of lower limits, the silica particles have a surface area greater than 0.01 m$^2$/g, e.g., greater than 0.02 m$^2$/g, greater than 0.04 m$^2$/g, greater than 0.6 m$^2$/g, greater than 0.08 m$^2$/g, greater than 0.1 m$^2$/g, greater than 0.15 m$^2$/g, or greater than 0.2 m$^2$/g. The inventors have found that silica particles have a low surface area compared to conventional fluidization aids which beneficially contributes to increased product yield. Advantageously, the silica particles have a lower porosity than conventional fluidization aids, e.g., alumina, which promotes product yield and selectively.

In some embodiments, the silica particles have a hardness ranging from 500 to 720 as measured by ASTM E384 (2018), e.g., from 510 to 700, from 520 to 680, from 540 to 640, from 550 to 620, from 560 to 600, or from 520 to 570. In terms of upper limits, the silica particles have a hardness less than 720, e.g., less than 700, less than 680, less than 660, less than 640, less than 620, less than 600, or less than 580. In terms of lower limits, the silica particles have a hardness greater than 510, e.g., greater than 515, greater than 520, greater than 525, greater than 530, greater than 540, greater than 550, greater than 560, or greater than 570. The inventors have found that silica particles have hardness values lower than conventional fluidization aids, e.g., alumina, thereby contributing to less erosion in the reactor.

In some aspects, the catalyst composition may further comprise other inerts, e.g., alumina. The manner in which the other inerts are provided in the catalyst composition may vary widely. Many techniques are within the contemplation of this disclosure and will be suitable, as long as the other inerts are ultimately present in the fluid bed. As one example, other inerts may be deposited in the fluid bed as a residue. For example, alumina particles may be present in the fluid bed from previous use of the fluid bed. In other aspects, a small quantity of other inerts may be added as a component of the inert additive composition, e.g., in a manner similar to that of the silica particles. In some aspects, the other inerts present in the fluid bed are entirely supplied as deposits in the fluid bed, e.g., a residue, and no other inert particles, e.g., inert additive, is separately added to the fluid bed.

In some embodiments, the inert additive composition comprises other inerts in an amount ranging from 0.5 wt % to 99.5 wt %, e.g., from 1 wt % to 99 wt %, from 2 wt % to 95 wt %, from 5 wt % to 90 wt %, from 10 wt % to 80 wt %, from 20 wt % to 70 wt %, from 30 wt % to 60 wt %, or from 40 wt % to 50 wt %, based on the total weight of the inert additive composition. In terms of upper limits, the inert additive composition comprises less than 99.5 wt % of other inerts, e.g., less than 99 wt %, less than 90 wt %, less than 80 wt %, less than 70 wt %, less than 60 wt %, less than 50 wt %, less than 40 wt %, or less than 30 wt %. In terms of lower limits, the inert additive composition comprises greater than 0.5 wt % of other inerts, e.g., greater than 1 wt %, greater than 2 wt %, greater than 5 wt %, greater than 10 wt %, greater than 12 wt %, greater than 15 wt %, greater than 20 wt %, or greater than 25 wt %. In some aspects, the catalyst composition and/or inert additive composition does not comprise other inerts, e.g., alumina.

In one embodiment, when other inerts are present in the catalyst composition, the weight ratio of other inerts to silica particles is in an amount ranging from 0.01:1 to 100:1, e.g., from 0.02:1 to 50:1, from 0.04:1 to 25:1, from 0.08:1 to 10:1, from 0.1:1 to 5:1, or from 0.2:1 to 1:1, based on the total weight of the catalyst composition. In terms of lower limits, the weight ratio of other inerts to silica particles may be greater than 0.01:1, e.g., greater than 0.02:1, greater than 0.03:1, greater than 0.04:1, greater than 0.05:1, greater than 0.1:1, greater than 0.2:1, or greater than 0.5:1. In terms of upper limits, the weight ratio of other inerts to silica particles may be less than 100:1, e.g., less than 80:1, less than 60:1, less than 40:1, less than 20:1, less than 10:1, or less than 1:1.

The catalyst composition may include a wide variety of catalysts that can be used to carry out different chemical reactions. The catalyst composition may comprise catalyst particles supported on a catalyst support. In some aspects, the catalyst support comprises silica. The silica in the catalyst support is separate from the silica particles in the inert additive composition, e.g., the silica support is not a fluidization aid.

In some embodiments, the catalyst comprises one or more of antimony, uranium, iron, bismuth, vanadium, molybdenum, potassium, nickel or cobalt in a catalytically active oxidized state. The catalyst may be individual oxides or salts of the elements in the selected catalyst. In some embodiments, the method of preparing the catalyst includes combining oxides, sulfates, or the like of antimony, uranium, iron, and bismuth with sulfuric acid. The catalyst can be shaped to suitable particle size having a desired surface area. In some aspects, the catalyst is an active catalyst that is suitable for the ammoxidation of propylene to acrylonitrile. The catalyst can be prepared by any known method.

In some embodiments, the fluidized bed in the reaction zone may comprise an active ammoxidation catalyst comprised of one or more of antimony, uranium, and iron along with possibly other metals such as bismuth and molybdenum. In some aspects, the catalyst is on a support. In embodiments where a support is used, the catalyst comprises from about 5 wt % to about 90 wt %, by weight of the catalyst. Any known support materials can be used, such as, silica, alumina, zirconia, alundum, silicon carbide, alumina-silica, and the inorganic phosphates, silicates, aluminates, borates, and carbonates which are stable under the reaction conditions in the feed reaction zone and do not significantly reduce the catalytic activity of the active portion of the catalyst.

In some embodiments, the catalyst composition may be specifically adapted for producing acrylonitrile product. For example, the catalyst mixed with the silica particles may be used to convert olefins with or without the presence of ammonia to produce acrylonitrile. The olefins employed as reactants for the conversion by the catalyst composition may be open chain, as well as cyclic and include, for example, propylene, butene-1, butene-2, isobutene, pentene-1 pentene-2, 3-methyl butene-1, 2-methyl butene-2, hexene-1, hexene-2, 4-methyl pentene-1, 3,3-dimethylbutene-1, 4-methyl pentene-2, octene-1, cyclopentene, cyclohexene and the like. In some aspects, mixtures of olefins and mixtures of olefins with other hydrocarbons may be employed in the fluid bed. In some aspects, when the catalyst composition described herein is used for ammoxidation, the olefins mentioned above are applicable. In some aspects, the fluid bed reactor system is adapted to convert a feed comprising propylene, ammonia, and oxygen to acrylonitrile.

In some embodiments, the catalyst composition may comprise a catalyst having an equivalent median diameter ranging from 1 microns to 125 microns, e.g., from 2 microns to 120 microns, from 4 microns to 110 microns, from 6 microns to 100 microns, from 10 microns to 80 microns, from 20 microns to 70 microns, from 30 microns to 60 microns, from 40 microns to 50 microns, or from 45 microns to 55 microns. In some aspects, the catalyst composition includes catalyst having an equivalent median diameter less than 125 microns, e.g., less than 120 microns, less than 110 microns, less than 100 microns, less than 90 microns, less than 80 microns, or less than 70 microns. In some aspects, the catalyst composition includes catalyst having an equivalent median diameter greater than 1 microns, e.g., greater than 2 microns, greater than 5 microns, greater than 10 microns, greater than 15 microns, greater than 20 microns, greater than 30 microns, greater than 40 microns, or greater than 50 microns.

In some embodiments, the combination of the silica particles and the catalyst in the fluid bed can synergistically improve product yield and reduce catalyst loss. For example, silica particles having at least one of the aforementioned properties, e.g., equivalent median particle diameter, density, surface area, hardness, etc., in combination with a catalyst with an equivalent median diameter ranging from 1 microns to 125 microns can improve product yield and reduce catalyst loss. In particular, using silica particles with a catalyst in a process for producing acrylonitrile was found to beneficially improve product yield and reduce catalyst loss. The catalyst can be one or more of antimony-iron based catalysts, molybdenum-bismuth based catalysts, iron based catalysts, antimony-iron based catalysts, and oxides thereof. Commercially available catalysts that are suitable include MAC-3 from Monsanto, Inc.

In some embodiments, the ratio of the equivalent median diameter of the silica particles to the equivalent median diameter of the catalyst is from 0.01:1 to 100:1, e.g., from 0.02:1 to 50:1, from 0.04:1 to 25:1, from 0.08:1 to 10:1, from 0.1:1 to 5:1, or from 0.2:1 to 1:1. In terms of lower limits, the ratio of the equivalent median diameter of the silica particles to the equivalent median diameter of the catalyst may be greater than 0.01:1, e.g., greater than 0.02:1, greater than 0.03:1, greater than 0.04:1, greater than 0.05:1, greater than 0.1:1, greater than 0.2:1, or greater than 0.5:1. In terms of upper limits, the ratio of the equivalent median diameter of the silica particles to the equivalent median diameter of the catalyst may be less than 100:1, e.g., less than 80:1, less than 60:1, less than 40:1, less than 20:1, less than 10:1, or less than 1:1.

In some aspects, the silica particles have an equivalent median particle diameter ranging from 10 microns to 500 microns, the silica particles have a surface area less than 50 m²/g, and the product yield is greater than 70%.

In some aspects, the silica particles have a real density ranging from 2.1 g/cm³ to 2.5 g/cm³, wherein the silica particles have a surface area less than 50 m²/g, the silica particles have a hardness ranging from 500 to 720 as measured by ASTM E384 (2018), and the product yield is greater than 70%.

In some aspects, the silica particles have an equivalent median particle diameter ranging from 20 microns to 100 microns, the silica particles have a real density ranging from 2.1 g/cm³ to 2.5 g/cm³, the silica particles have a sphericity greater than 67%, the silica particles have a hardness ranging from 500 to 720 as measured by ASTM E384 (2018), and the product yield is greater than 70%.

The inventors have found that utilizing silica particles in any fluid bed reactor provides the aforementioned benefits and improvements. For example, the process benefits can be seen in ammoxidation processes for producing nitriles or hydrogen cyanide, selective oxidation processes of hydrocarbons for producing carboxylic acid, aldehydes, or carboxylic anhydride, oxychlorination processes of hydrocarbon for producing vinyl chloride, fluid catalytic cracking (FCC) processes, fluid bed processes for polyethylene and/or polypropylene, and chemical looping combustion processes.

Fluid Bed Reactor System

In some embodiments, the present disclosure relates to reactor systems for preparing products, e.g., acrylonitrile. The reactor comprises a fluid bed including the catalyst composition and the inert additive composition described herein. In some embodiments, the reactor system may include one or more gas inlet feeds for passing gases upwardly through the fluid bed and one or more cyclones configured to separate particles from the gas flowing upwardly through the fluid bed of the reactor. The one or more cyclones are in communication with the upwardly flowing gas exiting the fluid bed.

In some embodiments, the reactor system comprises one or more cyclones that separates the catalyst composition and/or the inert additive composition entrained in the product stream as it exits the fluid bed. The cyclones separate and recover a major portion of the catalyst composition while the gaseous product stream passes overhead for further purification, utilization, or packaging. Unfortunately, in conventional reactor systems, a portion of the catalyst is converted to dust and exits the cyclone with the product stream.

The inventors have found that fluid bed reactor systems including silica particles having the aforementioned quantity, size, shape, density, etc., reduce the loss of catalyst compared to in an otherwise identical system not containing silica particles. The reduction in catalyst loss is realized when the fluid bed includes from 0.5 wt % to 30 wt % of silica particles, based on the total weight of the catalyst composition. It was found that cyclones had increased efficiency when separating the catalyst composition from the product stream when utilizing silica particles as a fluidization aid. For example, the silica particles contributed to an increased return of catalyst composition to the fluid bed from the cyclone. Without being bound by theory, it is believed that the similar density of the silica particles and the catalyst improves overall fluidization behavior, and contributes to an increased return of catalyst to the fluid bed. Additionally, it is believed that the specific particle size and shape of the silica particles reduce erosion in the cyclones compared to conventional fluidization aids.

In some embodiments, the reactor system includes from 1 to 10 cyclones, e.g., from 2 to 8, from 3 to 7, or from 4 to 6. In terms of upper limits, the reactor system includes less than 10 cyclones, e.g., less than 9, less than 8, less than 6, or less than 5. In terms of lower limits, the reactor system includes greater than 1 cyclone, e.g., greater than 2, greater than 3, greater than 4, or greater than 5. In some aspects, the number of cyclones may be increased until further separation is not possible or is impractical. In some aspects, the cyclones may be arranged in series.

In some embodiments, the cyclones may be located wholly within the reactor. In some aspects, the cyclone is mounted above the fluid bed to return the separated catalyst composition to the fluid bed via a discharge pipe. In some embodiments, each of the cyclones may include a discharge pipe to return the separated catalyst composition to the fluid bed. In some aspects, the last cyclone in a series of cyclones comprises a discharge pipe to return the separated catalyst composition to the fluid bed.

The inventors have also found that use of silica particles, e.g., with the specific density and particle size distribution, surprisingly and unexpectedly reduces erosion of the reactor system, e.g., the cyclones. In some embodiments, the silica particles reduce erosion of the reactor ranging from 10% to 70% compared to a similar process conducted without from 0.5 wt % to 30 wt % silica particles, e.g., from 15% to 65%, from 20% to 60%, from 25% to 55%, from 30% to 50%, or from 35% to 45%. In terms of lower limits, the silica particles reduce erosion of the reactor by greater than 10% compared to a similar process conducted without from 0.5 wt % to 30 wt % silica particles, e.g., greater than 15%, greater than 20%, greater than 25%, greater than 30%, greater than 35%, or greater than 40%.

Additionally, the inventors have also found that the shape of the silica particles contribute to reduced erosion in the cyclones. In some embodiments, silica particles having a sphericity ranging from 60% to 99.9% have been shown to reduce erosion in the cyclones, e.g., from 65% to 99%, from 70% to 95%, from 75% to 90%, from 80% to 90%, from 85% to 95%, or from 90% to 100%. In terms of lower limits, the silica particles have a sphericity greater than 60%, e.g., greater than 65%, greater than 67%, greater than 70%, greater than 75%, greater than 80%, greater than 85%, greater than 88%, greater than 90%, or greater than 90.5%. In terms of upper limits, the silica particles have a sphericity of less than 99.9%, e.g., less than 99%, less than 98% less than 96%, less than 95%, less than 94%, less than 92%, or less than 91%.

The FIGURE shows a schematic diagram of a fluid bed reactor system including a reactor system according to embodiments of the present disclosure. In the fluid bed reactor system 100, a feed of gaseous reactants can enter the system 100 through feed inlets 105, e.g., spargers, and pass through and fluidize a bed 110 of mixed catalyst and an inert additive composition comprising silica particles. The gaseous reactants can be fed independently to the fluid bed or can be pre-mixed before passing through the fluid bed.

The products, byproducts, unreacted reactants, and entrained particulates exit through conduit 115 into a first cyclone 120 where a major portion of the particulates are separated. Exit gas and unseparated particulates flow through top exit 124 into a second cyclone 130 for further separation of gas and solids. The separated solid particulates from the second cyclone 130 are returned to the fluid bed 110 via a discharge pipe 132. The remaining exit gas and unseparated particulates in the second cyclone 130 flow into a third cyclone 140 for further separation. The separated solid particulates from the third cyclone 140 are also returned to the fluid bed 110 via a discharge pipe 142. The number of cyclones may be increased until further separation is not possible or is impractical. For purposes of this description, the solids exiting the top of the last cyclone, e.g., the third cyclone 140, are considered lost or consumed catalyst.

In some embodiments, the feed provided to the fluid bed reactor system may comprise an olefin, ammonia, and an oxygen-containing gas. The components of the feed can be supplied independently to the fluid bed or can be co-mixed before being supplied to the fluid bed. For example, the olefin and the ammonia can be pre-mixed and supplied to the fluid bed, and the oxygen-containing gas, e.g., air, can be supplied independently to the fluid bed. In some embodiments, the molar ratio of oxygen to the olefin in the gas mixture ranges from 0.5:1 to 5:1, e.g., 1:1 to 4:1, from 2:1 to 3:1 or from 2.5:1 to 3.5:1. In terms of lower limits, the molar ratio of oxygen to the olefin in the feed is greater than 0.5:1, e.g., greater than 1:1, greater than 1.5:1, or greater than 2:1. In terms of upper limits, the molar ratio of oxygen to the olefin in the feed is less than 5:1, e.g., less than 4:1, less than 3:1, or less than 2.5:1.

In some embodiments, the molar ratio of ammonia to olefin in the gas mixture ranges from 0.5:1 to 5:1, e.g., 1:1 to 4:1, from 2:1 to 3:1 or from 2.5:1 to 3.5:1. In terms of lower limits, the molar ratio of ammonia to the olefin in the feed is greater than 0.5:1, e.g., greater than 1:1, greater than 1.5:1, or greater than 2:1. In terms of upper limits, the molar ratio of ammonia to the olefin in the feed is less than 5:1, e.g., less than 4:1, less than 3:1, or less than 2.5:1. While ammonia is most generally employed as the nitrogen providing compound, other nitrogen containing materials may be employed which chemically change to produce reactive nitrogen under the selected reaction conditions. Any source of oxygen, pure or in admixture with inert gases, may be employed in the process. In some embodiments, air can be used as a source of oxygen.

The silica particles in the inert additive composition effectively reduces consumption of the catalyst and/or reduces catalyst loss in a fluid bed reactor. For example, silica particles reduces consumption of the catalyst and/or catalyst loss in the fluid bed reactor compared to other fluidization aids, e.g., alumina. In some embodiments, the silica particles reduce consumption of catalyst in range from 5% to 30% per kilogram of product produced, e.g., from 6% to 28%, from 8% to 26%, from 10% to 24%, from 12% to 22%, from 14% to 20%, or from 16% to 18%. In terms of lower limits, the silica particles reduce consumption of catalyst by greater than 5% per kilogram of product produced, e.g., greater than 6%, greater than 8%, greater than 10%, greater than 12%, greater than 14%, or greater than 16%. In terms of upper limits, the silica particles reduce consumption of catalyst by less than 30% per kilogram of product produced, e.g., less than 28%, less than 26%, less than 24%, less than 22%, less than 20%, less than 18%. It was found that fluid bed reactors having silica particles in the fluid bed improves the overall life of the catalyst.

Beneficially, fluid bed processes that include inert additive compositions comprising silica also increase overall product yield. For example, silica particles improve product yield in fluid bed processes compared to other fluidization aids, e.g., alumina. In some embodiments, the process demonstrates a product yield increase ranging from 0.2% to 20% than that of a similar process conducted without from 0.5 wt % to 30 wt % silica particles, e.g., a product yield increase ranging from 0.4% to 18%, from 0.6% to 16%, from 0.8% to 14%, from 1% to 12%, from 2% to 10%, from 3% to 8%, or from 4% to 7%. In terms of lower limits, the process demonstrates a product yield greater than 0.2% greater than that of a similar process conducted without from 0.5 wt % to 30 wt % silica particles, e.g., greater than 0.2%, greater than 0.5%, greater than 1%, greater than 2%, greater than 3%, greater than 4%, greater than 5%, greater than 6%, greater than 7%, greater than 8%, greater than 9%, or greater than 10%. In terms of upper limits, the process demonstrates a product yield less than 20% greater than that of a similar process conducted without from 0.5 wt % to 30 wt % silica particles, e.g., less than 19% greater, less than 18% greater, less than 17% greater, less than 16% greater, less than 15% greater, less than 14% greater, less than 13% greater, less than 12% greater, or less than 11% greater.

EXAMPLES

The following examples describe the aspects of the process with reference to its use in an ammoxidation process for producing acrylonitrile. It is understood that the inventive concept is also applicable to other fluid bed systems.

The following examples were done in lab-scale reactors. In the following examples, inert additive compositions comprising silica particles were utilized as a fluidization aid in the fluid bed reactor. The silica particles had a particle size distribution as shown in Table 1 as determined by Microtrac S3500 (laser light scattering particle size analyzer). The silica particles had a surface area ranging from 0.25 $m^2/g$ to 0.35 $m^2/g$. The inert additive compositions comprised 99 wt % of $SiO_2$, 2500 ppm of $Al_2O_3$, 600 ppm of $Fe_2O_3$, 50 ppm of $Na_2O$, 100 ppm of $K_2O$, 100 ppm of CaO, and 100 ppm of MgO.

TABLE 1

| | Particle Size | |
|---|---|---|
| D-Values | Min (Microns) | Max (Microns) |
| 10% | 9.15 | 13.13 |
| 50% | 30.32 | 40.41 |
| 90% | 69.44 | 84.95 |

*D-value is diameter at which __% of sample's mass is comprised of particles less than the listed value.

The inert additive compositions were added to a fluid bed reactor containing a catalyst having the formula described in U.S. Pat. No. 6,916,763. Adjustments were made to the catalyst and inert additive compositions in the reactor to obtain a desired propylene conversion and provide the amounts of each shown in Table 2 below.

Comparative Example 1 utilized no fluidization aid (no alumina or silica) and Comparative Example 2 utilized 15 wt % of alumina.

A reaction mixture of propylene, air and ammonia was passed through the reactor at fluidization velocities. The exit stream from the reactor was divided and passed through separate sets of cyclones. The propylene conversion, total yield and selectivity of acrylonitrile and other products, coproducts, and byproducts are shown in Table 2. The propylene conversion, product selectivity and yields, and catalyst activity index (ACT IND) have the same the formula as those described in U.S. Pat. No. 6,916,763.

compositions comprising silica particles (5 wt. %) were utilized as a fluidization aid in the production-scale fluid bed reactors for Examples 7-9, and no inert additive compositions were utilized in Comparative Examples 4-6. The acrylonitrile yield for each comparative example was normalized to 100 and the acrylonitrile yield for each respective example was normalized accordingly. The acrylonitrile yield increase was calculated from the normalized values.

TABLE 2

|  | Silica Wt % | Alumina Wt % | CO Yield % | HCN Yield % | $CO_2$ Yield % | ACR Yield % | ACN Yield % | Propylene Conv. % | AN Sel. % | AN Yield % | Δ Sel. | ACT IND | Catalyst Charge (g) |
|---|---|---|---|---|---|---|---|---|---|---|---|---|---|
| Comp. 1 | 0 | 0 | 4.70 | 7.58 | 7.63 | 0.22 | 0.35 | 98.98 | 79.31 | 78.50 | 0.67 | 1.21 | 380 |
| Comp. 2 | 0 | 15 | 4.84 | 7.94 | 7.71 | 0.10 | 0.19 | 98.83 | 78.98 | 78.06 | 0.07 | 1.17 | 380 |
| Ex. 1 | 10 | 0 | 4.53 | 6.84 | 7.46 | 0.14 | 0.29 | 99.08 | 80.57 | 79.82 | 2.13 | 1.23 | 380 |
| Ex. 2 | 15 | 0 | 4.39 | 6.63 | 7.40 | 0.14 | 0.31 | 98.95 | 80.94 | 80.09 | 2.25 | 1.21 | 376 |
| Ex. 3 | 20 | 0 | 4.36 | 6.54 | 7.39 | 0.14 | 0.31 | 99.00 | 81.07 | 80.26 | 2.46 | 1.22 | 376 |

It was surprisingly found that the inert additive compositions comprising silica particles improved acrylonitrile yield and selectively compared to fluid bed processes that utilized no fluidization aid or just alumina as a fluidization aid. For example, each of Examples 1-3 utilized from 10 wt % to 20 wt % silica, based on the total weight of the catalyst composition, and had greater acrylonitrile yield and selectivity than both Comparative Examples 1 and 2. Beneficially, the silica particles also reduced the yield of byproducts, e.g., CO, HCN, $CO_2$, and ACR. Additionally, the examples show the acrylonitrile yields and selectivity increased when using silica particles in the fluid bed compared to a similar process using alumina particles at 15 wt %. In fact, using alumina particles at 15 wt % (Comparative Example 2) reduced acrylonitrile yield compared to a process that used no fluidization aid (Comparative Example 1). The specific weight percentage of silica particles in the fluid bed contributed to increased conversion of the reactants and overall yield of the process compared to alumina particles.

Table 3 shows propylene conversion, total yield and selectivity of acrylonitrile using an aged catalyst in a fluid bed process utilizing inert additive compositions comprising silica particles. Comparative 3 and Examples 4-6 utilized a used catalyst with different activity and age, e.g., used for certain number of years, than the catalyst used for the above examples, e.g., fresh catalyst.

TABLE 3

|  | Silica Wt % | CO Yield % | HCN Yield % | $CO_2$ Yield % | ACR Yield % | ACN Yield % | Propylene Conv. % | AN Sel. % | AN Yield % | Δ Sel. | ACT IND | Catalyst Charge (g) |
|---|---|---|---|---|---|---|---|---|---|---|---|---|
| Comp. 3 | 0 | 5.19 | 8.16 | 7.61 | 0.24 | 0.32 | 99.04 | 78.28 | 77.53 | −0.23 | 0.96 | 495 |
| Ex. 4 | 10 | 4.93 | 8.08 | 8.02 | 0.20 | 0.19 | 99.07 | 78.39 | 77.66 | −0.06 | 0.95 | 495 |
| Ex. 5 | 15 | 4.84 | 7.98 | 8.04 | 0.19 | 0.19 | 99.12 | 78.57 | 77.88 | 0.32 | 0.96 | 495 |
| Ex. 6 | 20 | 4.70 | 7.70 | 7.96 | 0.23 | 0.19 | 98.86 | 78.98 | 78.08 | 0.12 | 0.92 | 495 |

Generally, the silica particles used with aged catalyst still achieved good acrylonitrile yield and selectivity. Surprisingly, Examples 4-6 show that using silica particles in fluid bed processes improved acrylonitrile yield even with less active catalyst.

Examples 7-9 and Comparative Examples 4-6 were performed in separate production-scale fluid bed reactors. A reaction mixture of propylene, air and ammonia was passed through the reactor at fluidization velocities. Inert additive

TABLE 4

|  | Silica Fines (wt. %) | Normalized AN Yield (%) | AN yield increase (%) |
|---|---|---|---|
| Comp. 4 | 0 | 100.0 | 1.20% |
| Example 7 | 5 | 101.2 |  |
| Comp. 5 | 0 | 100.0 | 1.00% |
| Example 8 | 5 | 101.0 |  |
| Comp. 6 | 0 | 100.0 | 0.70% |
| Example 9 | 5 | 100.7 |  |

In each of Examples 7-9, the total acrylonitrile yield increased by at least 0.70% compared to the respective Comparative Example. The silica particles improved acrylonitrile yield compared to fluid bed processes that utilized no fluidization aid. For example, each of Examples 7-9 demonstrated improved acrylonitrile yield compared to respective Comparative Examples 4-6.

EMBODIMENTS

The following embodiments are contemplated. All combinations of features and embodiments are contemplated.

Embodiment 1

A process comprising: reacting one or more reactants in a reactor comprising a fluid bed to form a product; wherein the fluid bed comprises a catalyst composition comprising a catalyst and an inert additive composition comprising from 0.5 wt % to 30 wt % of silica particles, based on the total weight of the catalyst composition.

Embodiment 2

An embodiment of embodiment 1, wherein the silica particles have an equivalent median particle diameter ranging from 10 microns to 500 microns.

Embodiment 3

An embodiment of embodiments 1 or 2, wherein the silica particles have a real density ranging from 1.8 g/cm$^3$ to 2.8 g/cm$^3$.

Embodiment 4

An embodiment of any of embodiments 1-3, wherein the difference between the density of the silica particles and the catalyst is less than 75%.

Embodiment 5

An embodiment of any of embodiments 1-4, wherein the catalyst has an equivalent median particle diameter ranging from 1 microns to 125 microns.

Embodiment 6

An embodiment of any of embodiments 1-5, wherein the catalyst composition further comprises alumina particles.

Embodiment 7

An embodiment of any of embodiments 1-6, wherein a weight ratio of alumina particles to silica particles is less than 1:1.

Embodiment 8

An embodiment of any of embodiments 1-7, wherein the silica particles have a surface area less than 50 m$^2$/g.

Embodiment 9

An embodiment of any of embodiments 1-8, wherein the silica particles have a hardness ranging from 500 to 720 as measured by ASTM E384 (2018).

Embodiment 10

An embodiment of any of embodiments 1-9, wherein the inert additive composition comprises no alumina.

Embodiment 11

An embodiment of any of embodiments 1-10, wherein the process reduces consumption of the catalyst by greater than 5% per kilogram of product produced compared to other fluidization aids.

Embodiment 12

An embodiment of any of embodiments 1-11, wherein the silica particles reduce erosion of the reactor by greater than 10% compared to a similar process conducted without from 0.5 wt % to 30 wt % silica particles.

Embodiment 13

An embodiment of any of embodiments 1-12, wherein the process demonstrates a product yield greater than 0.2% greater than that of a similar process conducted without from 0.5 wt % to 30 wt % silica particles.

Embodiment 14

An embodiment of any of embodiments 1-13, wherein the silica particles are mixed with the catalyst in the fluid bed.

Embodiment 15

An embodiment of any of embodiments 1-14, wherein the silica particles comprise greater than 99 wt % silica.

Embodiment 16

An embodiment of any of embodiments 1-15, wherein the silica particles comprise impurities ranging from 0.01 wt % to 20 wt %.

Embodiment 17

An embodiment of any of embodiments 1-16, wherein the silica particles comprise less than 180 ppm of iron and less than 150 ppm of nickel.

Embodiment 18

An embodiment of any of embodiments 1-17, wherein the silica particles have an equivalent median particle diameter ranging from 10 microns to 500 microns, wherein the silica particles have a surface area less than 50 m$^2$/g, and wherein the product yield is greater than 70%.

Embodiment 19

An embodiment of any of embodiments 1-18, wherein the silica particles have a real density ranging from 2.1 g/cm$^3$ to 2.5 g/cm$^3$, wherein the silica particles have a surface area less than 1 m$^2$/g, wherein the silica particles have a hardness ranging from 500 to 720 as measured by ASTM E384 (2018), wherein the product yield is greater than 70%.

Embodiment 20

An embodiment of any of embodiments 1-19, wherein the silica particles have an equivalent median particle diameter ranging from 20 microns to 100 microns, wherein the silica particles have a real density ranging from 2.1 g/cm$^3$ to 2.5 g/cm$^3$, wherein the silica particles have a sphericity greater than 67%, wherein the silica particles comprise greater than 99 wt % silica, wherein the product yield is greater than 70%.

Embodiment 21

An embodiment of any of embodiments 1-20, wherein the catalyst comprises one or more of molybdenum, bismuth, antimony, iron, uranium, silicon dioxide or mixtures thereof.

Embodiment 22

A process for producing acrylonitrile product, the process comprising: reacting one or more reactants in a reactor comprising a fluid bed to form an acrylonitrile product; wherein the fluid bed comprises a catalyst composition comprising a catalyst and an inert additive composition comprising from 0.5 wt % to 30 wt % of silica particles, based on the total weight of the catalyst composition.

Embodiment 23

An embodiment of embodiment 22, wherein the silica particles have an equivalent median particle diameter ranging from 10 microns to 500 microns.

Embodiment 24

An embodiment of any of embodiments 22 or 23, wherein the process demonstrates an acrylonitrile product yield greater than 0.2% greater than that of a similar process conducted without from 0.5 wt % to 30 wt % silica particles.

Embodiment 25

An embodiment of any of embodiments 22-24, wherein the one or more reactants comprises an olefin, ammonia, and an oxygen-containing gas.

Embodiment 26

An embodiment of any of embodiments 22-25, wherein the reactor further comprises: one or more gas inlet feeds for passing the one or more reactants upwardly through the fluid bed; and one or more cyclones configured to separate particles from the gas flowing upwardly through the fluid bed of the reactor, the one or more cyclones being in communication with the upwardly flowing gas exiting the fluid bed.

Embodiment 27

An embodiment of embodiment 26, wherein the one or more cyclones comprise a particle discharge pipe for returning separated particles to the fluid bed.

Embodiment 28

A reactor system for preparing acrylonitrile product, comprising: a fluid bed comprising a catalyst composition comprising a catalyst and an inert additive composition comprising from 0.5 wt % to 30 wt % of silica particles, based on the total weight of the catalyst composition; and one or more gas inlet feeds for passing one or more reactants upwardly through the fluid bed to form an acrylonitrile product.

Embodiment 29

An embodiment of embodiment 28, wherein the silica particles have an equivalent median particle diameter ranging from 10 microns to 500 microns.

Embodiment 30

An embodiment of any of embodiments 28 or 29, wherein the silica particles have a real density ranging from 1.8 g/cm$^3$ to 2.8 g/cm$^3$, wherein the silica particles have a surface area less than 50 m$^2$/g, and wherein the silica particles have a hardness ranging from 500 to 720 as measured by ASTM E384 (2018).

Embodiment 31

An embodiment of any of embodiments 28-30, wherein the silica particles have a real density ranging from 2.1 g/cm$^3$ to 2.5 g/cm$^3$, wherein the silica particles have a surface area less than 1 m$^2$/g, wherein the silica particles comprise greater than 99 wt % silica, wherein the product yield is greater than 70%.

Embodiment 32

An embodiment of any of embodiments 28-31, wherein the process demonstrates an acrylonitrile product yield greater than 0.2% greater than that of a similar process conducted without from 0.5 wt % to 30 wt % silica particles.

Embodiment 33

An embodiment of any of embodiments 28-32, wherein the silica particles reduce erosion of the reactor by greater than 10% compared to a similar process conducted without from 0.5 wt % to 30 wt % silica particles.

Embodiment 34

An embodiment of any of embodiments 28-33, wherein the reactor system further comprises: one or more gas inlet feeds for passing the one or more reactants upwardly through the fluid bed; and one or more cyclones to separate particles from the gas flowing upwardly through the fluid bed of the reactor, the cyclones being in communication with the upwardly flowing gas exiting the fluid bed.

Embodiment 35

An embodiment of embodiment 34, wherein the one or more cyclones comprise a particle discharge pipe for returning separated particles to the fluid bed.

Embodiment 36

A process comprising: reacting one or more reactants in a reactor comprising a fluid bed to form a product; wherein the fluid bed comprises a catalyst composition comprising a catalyst and an inert additive composition comprising from 0.5 wt % to 30 wt % of silica particles, based on the total weight of the catalyst composition, wherein the silica particles have an equivalent median particle diameter ranging from 10 microns to 500 microns.

Embodiment 37

An embodiment of embodiment 36, wherein the catalyst comprises one or more of antimony, uranium, iron, bismuth, vanadium, molybdenum, nickel, potassium, cobalt, oxides thereof, or salts thereof.

Embodiment 38

An embodiment of embodiment 36, wherein the catalyst has an equivalent median diameter ranging from 1 microns to 125 microns.

Embodiment 39

An embodiment of embodiment 36, wherein the silica particles have a real density ranging from 1.8 g/cm$^3$ to 2.8 g/cm$^3$, and wherein the difference between the density of the silica particles and the catalyst is less than 75%.

Embodiment 40

An embodiment of embodiment 36, wherein the silica particles have a surface area less than 50 m$^2$/g, and wherein the silica particles have a hardness ranging from 500 to 720 as measured by ASTM E384 (2018).

Embodiment 41

An embodiment of embodiment 36, wherein the silica particles have a sphericity ranging from 60% to 99.9%

Embodiment 42

An embodiment of embodiment 36, wherein the catalyst composition further comprises alumina particles, wherein a weight ratio of alumina particles to silica particles is less than 1:1.

Embodiment 43

An embodiment of embodiment 36, wherein the inert additive composition comprises no alumina.

Embodiment 44

An embodiment of embodiment 36, wherein the process reduces consumption of the catalyst by greater than 5% per kilogram of product produced compared to other fluidization aids.

Embodiment 45

An embodiment of embodiment 36, wherein the silica particles reduce erosion of the reactor by greater than 10% compared to a similar process conducted without from 0.5 wt % to 30 wt % silica particles.

Embodiment 46

An embodiment of embodiment 36, wherein the process demonstrates a product yield greater than 0.2% greater than that of a similar process conducted without from 0.5 wt % to 30 wt % silica particles.

Embodiment 47

An embodiment of embodiment 36, wherein the silica particles have a real density ranging from 2.1 g/cm$^3$ to 2.5 g/cm$^3$, wherein the silica particles have a surface area less than 1 m$^2$/g, wherein the silica particles have a hardness ranging from 500 to 720 as measured by ASTM E384 (2018), and wherein the product yield is greater than 70%.

Embodiment 48

An embodiment of embodiment 36, wherein the silica particles have an equivalent median particle diameter ranging from 20 microns to 100 microns, wherein the silica particles have a real density ranging from 2.1 g/cm$^3$ to 2.5 g/cm$^3$, wherein the silica particles have a sphericity greater than 67%, wherein the silica particles comprise greater than 99 wt % silica, wherein the product yield is greater than 70%.

Embodiment 49

A process for producing acrylonitrile product, the process comprising: reacting one or more reactants in a reactor comprising a fluid bed to form an acrylonitrile product; wherein the fluid bed comprises a catalyst composition comprising a catalyst and an inert additive composition comprising silica particles having a density from 1.8 g/cm$^3$ to 2.8 g/cm$^3$, wherein the silica particles have a sphericity ranging from 60% to 99.9%.

Embodiment 50

An embodiment of embodiment 49, wherein the difference between the density of the silica particles and the catalyst is less than 75%, wherein the process demonstrates an acrylonitrile product yield greater than 0.2% greater than that of a similar process conducted without silica particles.

Embodiment 51

An embodiment of embodiment 49, wherein the one or more reactants comprises an olefin, ammonia, and an oxygen-containing gas.

Embodiment 52

A reactor system for preparing acrylonitrile product, comprising: a fluid bed comprising a catalyst composition comprising a catalyst and an inert additive composition comprising from 0.5 wt % to 30 wt % of silica particles, based on the total weight of the catalyst composition; and one or more gas inlet feeds for passing one or more reactants upwardly through the fluid bed to form an acrylonitrile product, wherein the difference between the density of the silica particles and the catalyst particles ranges from 0.5% to 75%, wherein the silica particles reduce erosion of the reactor by greater than 10% compared to a similar process conducted without from 0.5 wt % to 30 wt % silica particles.

Embodiment 53

An embodiment of embodiment 52, wherein the silica particles have a real density ranging from 1.8 g/cm$^3$ to 2.8 g/cm$^3$, wherein the silica particles have a surface area less than 50 m$^2$/g, wherein the silica particles have a hardness ranging from 500 to 720 as measured by ASTM E384 (2018), and wherein the product yield is greater than 70%.

Embodiment 54

An embodiment of embodiment 52, wherein the process demonstrates an acrylonitrile product yield greater than 0.2% greater than that of a similar process conducted without from 0.5 wt % to 30 wt % silica particles.

Embodiment 55

An embodiment of embodiment 52, wherein the reactor system further comprises: one or more gas inlet feeds for passing the one or more reactants upwardly through the fluid bed; and one or more cyclones to separate particles from the gas flowing upwardly through the fluid bed of the reactor, the cyclones being in communication with the upwardly flowing gas exiting the fluid bed, wherein the one or more cyclones comprise a particle discharge pipe for returning separated particles to the fluid bed.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that embodiments of the invention and portions of various embodiments and various features recited herein and/or in the appended claims may be combined or interchanged either in whole or in part. In the foregoing descriptions of the various embodiments, those embodiments which refer to another embodiment may be appropriately combined with other embodiments as will be appreciated by one of skill in the art.

We claim:

1. A process comprising:
reacting one or more reactants in a reactor comprising a fluid bed to form a product;
wherein the fluid bed comprises a catalyst composition comprising a catalyst and an inert fluidization aid comprising from 0.5 wt % to 30 wt % of silica particles, based on the total weight of the catalyst composition,
wherein the silica particles have an equivalent median particle diameter ranging from 10 microns to 500 microns and a sphericity ranging from 60% to 99.9%.

2. The process of claim 1, wherein the catalyst comprises one or more of antimony, uranium, iron, bismuth, vanadium, molybdenum, nickel, potassium, cobalt, oxides thereof, or salts thereof.

3. The process of claim 1, wherein the catalyst has an equivalent median diameter ranging from 1 microns to 125 microns.

4. The process of claim 1, wherein the silica particles have a real density ranging from 1.8 g/cm$^3$ to 2.8 g/cm$^3$, and wherein the difference between the density of the silica particles and the catalyst is less than 75%.

5. The process of claim 1, wherein the silica particles have a surface area less than 50 m$^2$/g, and wherein the silica particles have a hardness ranging from 500 to 720 as measured by ASTM E384 (2018).

6. The process of claim 1, wherein the catalyst composition further comprises alumina particles, wherein a weight ratio of alumina particles to silica particles is less than 1:1.

7. The process of claim 1, wherein the fluidization aid comprises no alumina.

8. The process of claim 1, wherein the process reduces consumption of the catalyst by greater than 5% per kilogram of product produced, as compared to an otherwise identical process using fluidization aids other than the silica particles.

9. The process of claim 1, wherein the silica particles reduce erosion of the reactor by greater than 10% compared to an otherwise identical a similar process conducted without from 0.5 wt % to 30 wt % of the silica particles.

10. The process of claim 1, wherein the process demonstrates a product yield greater than 0.2% greater than that of an otherwise identical a similar process conducted without from 0.5 wt % to 30 wt % of the silica particles.

11. The process of claim 1, wherein the silica particles have a real density ranging from 2.1 g/cm$^3$ to 2.5 g/cm$^3$, wherein the silica particles have a surface area less than 1 m$^2$/g, wherein the silica particles have a hardness ranging from 500 to 720 as measured by ASTM E384 (2018), and wherein the product yield is greater than 70%.

12. The process of claim 1, wherein the silica particles have an equivalent median particle diameter ranging from 20 microns to 100 microns, wherein the silica particles have a real density ranging from 2.1 g/cm$^3$ to 2.5 g/cm$^3$, wherein the silica particles have a sphericity greater than 67%, wherein the silica particles comprise greater than 99 wt % silica, wherein the product yield is greater than 70%.

13. A process for producing an acrylonitrile product, the process comprising:
reacting one or more reactants in an ammoxidation reactor comprising a fluid bed under ammoxidation conditions to form the acrylonitrile product;
wherein the fluid bed comprises a catalyst composition comprising a catalyst and an inert fluidization aid silica particles having a density from 1.8 g/cm$^3$ to 2.8 g/cm$^3$,
wherein the silica particles have a sphericity ranging from 60% to 99.9%.

14. The process of claim 13, wherein the difference between the density of the silica particles and the catalyst is less than 75%, wherein the process demonstrates an acrylonitrile product yield greater than 0.2% greater than that of an otherwise identical process conducted without the silica particles.

15. The process of claim 13, wherein the one or more reactants comprises an olefin, ammonia, and an oxygen-containing gas.

* * * * *